United States Patent [19]
Dietz et al.

[11] Patent Number: 5,310,472
[45] Date of Patent: May 10, 1994

[54] SENSOR ELEMENT FOR LIMITING CURRENT SENSORS TO DETERMINE THE LAMBDA VALUE OF GAS MIXTURES

[75] Inventors: Hermann Dietz; Werner Grünwald, both of Gerlingen; Claudio de la Prieta, Stuttgart, all of Fed. Rep. of Germany

[73] Assignee: Robert Bosch GmbH, Stuttgart, Fed. Rep. of Germany

[21] Appl. No.: 700,141
[22] PCT Filed: Nov. 17, 1989
[86] PCT No.: PCT/DE89/00731
  § 371 Date: May 16, 1991
  § 102(e) Date: May 16, 1991
[87] PCT Pub. No.: WO90/06506
  PCT Pub. Date: Jun. 14, 1990

[30] Foreign Application Priority Data

Dec. 10, 1988 [DE] Fed. Rep. of Germany ....... 3841611

[51] Int. Cl.$^5$ .......................................... G01N 27/419
[52] U.S. Cl. ................................... 204/425; 204/426; 204/429
[58] Field of Search ................... 204/153.18, 421–429

[56] References Cited

U.S. PATENT DOCUMENTS

| | | | |
|---|---|---|---|
| 4,502,939 | 3/1985 | Holfelder et al. | 284/427 |
| 4,724,061 | 2/1988 | Nyberg | 204/427 |
| 4,810,529 | 3/1989 | Mantese et al. | 204/429 |
| 4,816,749 | 3/1989 | Schmidtpott et al. | 204/427 |

FOREIGN PATENT DOCUMENTS

| | | |
|---|---|---|
| 1248198 | 1/1989 | Canada . |
| 0191627A1 | 8/1986 | European Pat. Off. . |
| 310498 | 8/1982 | Fed. Rep. of Germany . |
| WO89/02073 | 3/1989 | World Int. Prop. O. . |
| WO89/02074 | 3/1989 | World Int. Prop. O. . |
| WO89/08840 | 9/1989 | World Int. Prop. O. . |

*Primary Examiner*—T. Tung
*Attorney, Agent, or Firm*—Frishauf, Holtz, Goodman & Woodward

[57] ABSTRACT

Sensor element for limiting current sensors to determine the lambda value of gas mixtures, in particular of exhaust gases of internal combustion engines, having inner and outer pump electrodes disposed on a ceramic substrate, the inner pump electrode of which is accessible for the measurement gas supplied through a diffusion layer acting as a diffusion barrier; having a gas-tight cover layer above the diffusion layer and having conductor tracks for the pump electrodes is described, in which the diffusion layer is adjustable, to calibrate the sensor element. This adjustability is advantageously attained by embodying the side of the diffusion layer 5 oriented toward the measurement gas inlet opening as a zigzag-shaped adjustment zone 8, from which parts can be separated mechanically or by laser cuts. The invention makes comparatively simple calibration of sensor elements possible.

18 Claims, 1 Drawing Sheet

SENSOR ELEMENT FOR LIMITING CURRENT SENSORS TO DETERMINE THE LAMBDA VALUE OF GAS MIXTURES

PRIOR ART

The invention is based on a sensor element for limiting current sensors. In such sensor elements, which operate by the diffusion limiting current principle, the diffusion limiting current is generally measured at a constant voltage applied to both electrodes of the sensor element. In exhaust gas produced in combustion processes, current is dependent on the oxygen concentration, as long as the diffusion of the gas to the pump electrode determines the speed of the electrode reaction taking place. It is known to structure such sensors, which operate by the polarographic measuring principle, in such a way that both the anode and the cathode are exposed to the gas to be measured; the cathode has a diffusion barrier, to enable operating in the diffusion limiting current range.

As a rule, the known limiting current sensors serve to determine the lambda value of exhaust gas mixtures, which expresses the ratio between total oxygen and the oxygen required for complete combustion of the fuel in the fuel/air mixture burning in a cylinder.

Because of its simplified and relatively inexpensive manufacture, the production of probes and sensor elements that can be made by ceramic foil and screenprinting techniques has become established in the industry in recent years.

Planar polarographic probes can be produced simply and economically beginning with oxygen-carrying solid electrolytes in the form of small plates or foils, for instance of stabilized zirconium dioxide, which are coated on both sides with an (inner or outer) pump electrode and with the associated conductor track. The inner pump electrode is advantageously located at the end of a diffusion gap or diffusion channel, through which the measurement gas can diffuse in, and which serves as a gas diffusion resistor.

Sensor elements and detectors are also known from German Patent Disclosure Document 35 43 759 and from European Patent Applications 0 142 992, 0 142 993, 0 188 900 and 0 194 082, which have in common the fact that they each have a pump cell and a sensor cell, which comprise oxygen-carrying solid electrolytes in the form of small plates or foils, and two electrodes disposed on them, and have a common diffusion gap or diffusion channel.

German Patent Disclosure Document 38 34 987 also describes a sensor element for limiting current sensors for determining the lambda value of gas mixtures, in particular the exhaust gases of internal combustion engines, having a pair of pump electrodes disposed on a solid electrolyte that conducts $O^{2-}$-ions, in which the inner pump electrode communicates with the measurement gas via a diffusion gap, and the diffusion gap is covered by a solid electrolyte layer produced by screenprinting.

A disadvantage of the known sensor elements, which are in particular manufactured by laminating a plurality of solid electrolyte foils together, particularly those based on stabilized $ZrO_2$, is that a later change in the geometry of the diffusion layer, for instance for the sake of calibrating the sensor elements once the sensor elements have been finally sintered together, is as a rule difficult. The magnitude of the diffusion current in limiting current sensors in fact depends on the shaping of the diffusion layer, which can be made by various methods. In ceramic probes, such diffusion barriers are preferably applied to unsintered ceramic substrates by screenprinting and the entire assembly is then sintered. Only then can the limiting current be measured.

To preclude this disadvantage, it is known, for instance from European Patent Application 0 191 627, to use sensor elements having adjustable resistors on the sensor body. However, this has the disadvantage that manufacturing such a sensor element is comparatively complicated and expensive, and that additional electric leads are needed for this purpose on the sensor body.

ADVANTAGES OF THE INVENTION

The sensor element according to the invention has the substantial advantage over the element known from European Patent Application 0 191 627 that it is simpler to manufacture and that fewer electrical leads are needed. In the case of a sensor element according to the invention, varying the diffusion resistance of the finished sensor element is possible within wide limits, by successively expanding the inlet opening of the gas into the diffusion layer mechanically or by means of laser cuts. This is made possible by zigzag contouring of the diffusion layer at its end at which the measuring gas inlet opening is provided. If as a result the diffusion resistance of a finished sensor element is too high for it to operate in a favorable load range, then a portion of the adjustment zone is severed mechanically or by laser cuts. The number, length and spacing of the zigzags from one another are selected such that the pump electrode can operate in a favorable load range, in accordance with the quantity of diffused-in measurement gas.

Mechanical severing of parts of the adjustment zone is suitably done in such a way that the limiting current is set to a defined value during ongoing measurement, by sandblasting or by means of a ceramic saw; because of the mechanical machining, the tunnel inputs, such as the tunnel inputs shown in FIG. 2 formed by the adjustment zone 8 of the diffusion layer 5, are expanded.

When parts of the adjustment zone are severed by laser cuts, the procedure is equivalent, in that the tunnel inputs are opened by laser cuts until a defined limiting current flows.

The geometry of the diffusion layer is adapted to the given factors in an individual case. This means that the diffusion layer can take very different forms and have quite different measurements.

In the case of rectangular electrodes, for instance, it can cover the electrodes geometrically similarly, or in the case of round electrodes it can encompass them circularly. The number, length and spacing of the zigzags from one another are selected in such a way, preferably as a function of the available electrode surface area, that the electrodes can operate in a favorable load range in accordance with the diffused-in quantity of gas.

The sensor element according to the invention can be used in limiting current sensors of the conventional type, instead of known sensor elements of planar structure. Possible examples include wide band sensors (lambda less than, greater than, or equal to one) and lean sensors (lambda > 1). The sensor element according to the invention can thus be embodied by itself as a pump element, optionally with a heating element, for instance as a lean sensor for Diesel engines, and as such can be installed into a typical sensor housing, for instance the type known from German Patent Disclosure Documents 32 06 903 and 35 37 051, and used to measure the fuel/air ratio in a lean or rich exhaust gas. However, in addition to the pump cell, the sensor element according to the invention can additionally have a sensor cell (Nernst cell), which is provided with an additional air reference channel, and one electrode of which is disposed in the region of the pump electrode in the diffusion channel of the pump cell, and the other electrode of which is located in the air reference channel.

DRAWING

Advantageous embodiments of a sensor element according to the invention are shown by way of example in the drawing. Specifically, shown are in:

FIG. 1, a first embodiment of a sensor element according to the invention, in a schematic sectional view;

FIG. 2, the shape of a diffusion layer, shown schematically in a plan view; and

FIG. 3, a second embodiment of a sensor element, seen in a schematic sectional view.

DESCRIPTION OF THE EXEMPLARY EMBODIMENTS

Figure 1:
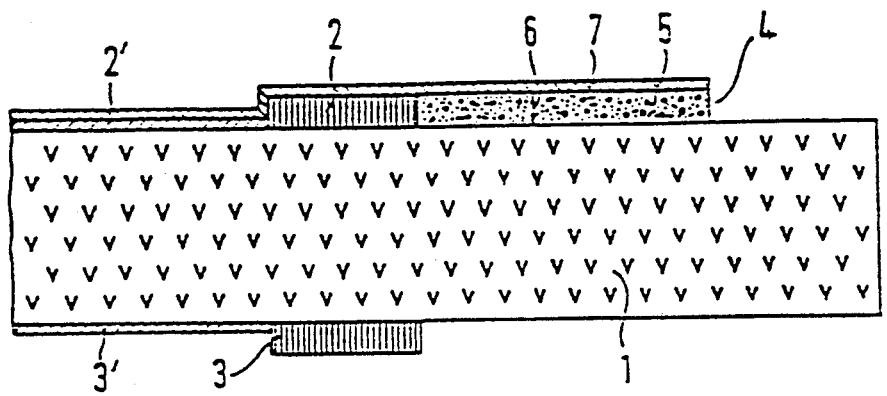

The sensor element schematically shown in FIG. 1 comprises the ceramic substrate 1, onto which the inner pump electrode (cathode) 2 with the conductor track 2' and the outer pump electrode (anode) 3 with the conductor track 3' are applied. The inner pump electrode 2 is supplied with measurement gas via the measurement gas inlet 4 and the diffusion gap 6 which is filled with the diffusion layer 5. The pump electrode 2, conductor track 2' and diffusion layer 5 are covered by the gas-tight cover layer 7.

Figure 2:
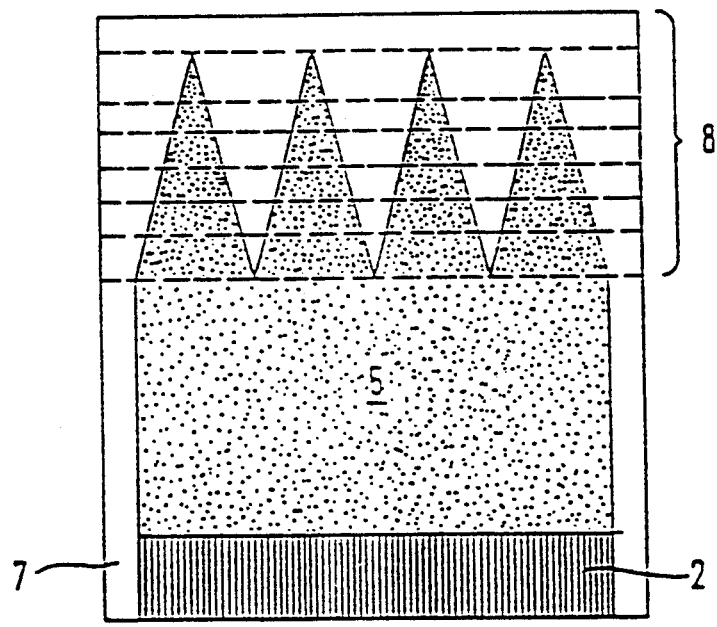

FIG. 2 shows the geometrical shape of the diffusion layer 5 with the zigzag-shaped adjustment zone 8. The dashed lines represent regions that can for instance be severed.

Figure 3:
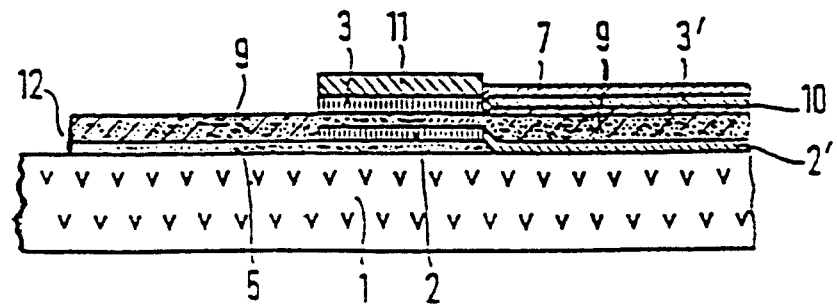

The sensor element schematically shown in FIG. 3 comprises the ceramic substrate 1, the inner pump electrode 2 with the associated conductor track 2', the diffusion layer 5, the solid electrolyte layer 9, the outer pump electrode 3 with the associated conductor track 3', the insulation layer 10, the engobe 11 and the cover layer 7. The entry of measurement gas takes place at 12. The diffusion layer 5 can also have a geometrical shape such as that shown by way of example in FIG. 2.

The porous diffusion layers 5 acting as diffusion barriers can be printed onto the unsintered ceramic substrate by screenprinting, using typical printing pastes. However, it is also possible to print heat-eroded layers onto the unsintered ceramic substrate and to sinter the entire assembly layer. Foils of suitable geometric shape that sinter in porous fashion can also be used to embody the diffusion layer.

Advantageously, the diffusion layer 5 and the adjustment zone 8 comprise a ceramic material that sinters in a coarsely porous fashion, such as one based on $Al_2O_3$ or $ZrO_2$. The porosity of the diffusion layer can be set by the addition of pore formers, which burn, decompose or evaporate in the sintering process. Typical pore formers that can be used include, for example, thermal soot powder; plastics, for instance based on polyurethane; salts, such as ammonium carbonate; and organic substances, such as theobromine and indanthrene blue. Such pore formers are added to the porously sintering starting material in a quantity such that a material having a porosity of 10 to 50%, for instance, is produced.

The mean pore diameter, which can be determined by the particle size of the pore former used, is preferably in the range of approximately 0.1 to 10 micrometers.

Advantageously, the diffusion layer 5 can further be embodied such that both Knudsen and gas-phase diffusion take place. This means that the diffusion layer forming the diffusion barrier has a channel system for mixed diffusion comprising both Knudsen and gas-phase diffusion, as described in further detail in German Patent Disclosure Document 37 28 289.

The ceramic substrate 1 comprises a ceramic material of the kind typically used to produce sensor elements, for instance based on $ZrO_2$ or $Al_2O_3$. Preferably the ceramic substrate 1 comprises one of the known oxides, used to make solid electrolyte foils that conduct $O^{2-}$ ions, of quadrivalent metals, such as $ZrO_2$, $CeO_2$, $HfO_2$ and $ThO_2$ in particular, having a content of bivalent alkaline earth oxides and/or preferably trivalent rare earth oxides. Typically, the layer can comprise up to 50 to 97 Mol % $ZrO_2$, $CeO_2$, $HfO_2$ or $ThO_2$ and 50 to 3 Mol % CaO, MgO or SrO, and/or oxides of rare earths and in particular $Y_2O_3$. It has proved advantageous to manufacture the sensor elements in the form of ceramic substrates, to use foils of unsintered ceramic material with a layer thickness of from 0.3 to 1.0 mm and in particular approximately 0.5 mm.

The pump electrodes 2 and 3 and the associated conductor tracks 2' and 3' preferably comprise a metal of the platinum group, in particular platinum, or alloys of metals of the platinum group or alloys of metals of the platinum group with other metals. Optionally, they contain a ceramic support structure material, for instance in the form of a YSZ powder, having a volumetric proportion of preferably approximately 40 volume %. They are porous and as thin as possible. Preferably, they have a thickness of 8 to 15 micrometers. The conductor tracks belonging to the pump electrodes preferably likewise comprise platinum or a platinum alloy of the type described. They may also be produced beginning with a paste based on noble metal and cermet.

Pastes suitable for printing the pump electrodes and conductor tracks can be prepared in a known manner, using organic binders and/or adhesion promoters, plasticizers and organic solvents. If insulating intermediate layers are to be produced simultaneously as well, then lesser quantities of compounds having a pentavalent or higher valent cation, such as $Nb_2O_5$, can be added to the pastes. $Al_2O_3$ or $ZrO_2$ are suitable as adhesion-promoting additives.

The gas-tight cover layer 7 for instance comprises a layer based on $Al_2O_3$ or Mg-spinel, as is typically used in planar sensor elements to cover electrodes In the case of the embodiment shown by way of example in FIG. 3 of a sensor element according to the invention, the solid electrolyte layer 9 comprises one of the known oxides, used for producing solid electrolyte foils that conduct $O^{2-}$ ions, of quadrivalent metals, such as $ZrO_2$, $CeO_2$, $HfO_2$ and $ThO_2$, in particular, having a content of bivalent alkaline earth oxides and/or preferably trivalent rare earth oxides. Typically, the layer can comprise approximately 50 to 97 Mol % $ZrO_2$, $CeO_2$, $HfO_2$ or $ThO_2$, and 50 to 3 Mol % CaO, MgO or SrO, and/or oxides of rare earths and in particular $Y_2O_3$. Advantageously, the layer comprises $ZrO_2$ stabilized with $Y_2O_3$. The thickness of the layer can advantageously range from 10 to 200 micrometers, in particular 15 to 50 micrometers.

The pastes used to produce the solid electrolyte layer can be produced using binders and/or adhesion promoters, plasticizers and organic solvents.

The insulation layer 10, which insulates the conductor track 3' of the outer pump electrode 3 from the solid electrolyte layer 9, comprises an insulating layer, for instance based on $Al_2O_3$, such as that typically produced in the production of planar sensor elements, for insulating conductor tracks from a solid electrolyte. The insulation layer 10 may for instance be 15 to 20 micrometers thick.

Optionally, such an insulation layer can also be disposed between the substrate 1 and the conductor track 2' of the inner pump electrode 2, for instance in the case in which the substrate is a solid-electrolyte-based substrate, such as a $ZrO_2$ substrate. The disposition of such insulation layers is not absolutely necessary, however.

The engobe 11 is porous and for instance comprises a layer based on $Al_2O_3$ or Mg-spinel, as is typically used in planar sensor elements to cover electrodes. The thickness of the engobe is for instance in the range from 10 to 40 micrometers.

In an advantageous embodiment of the invention, the porous engobe comprises an $Al_2O_3$ and/or Mg-spinel matrix, with $ZrO_2$ particles embedded in it, of the type known from German Patent Disclosure Document 37 37 215.

EXAMPLE

To produce a sensor element of the type schematically shown in FIG. 3, a foil of zirconium dioxide, stabilized with yttrium, having a layer thickness of 0.5 mm, was used as the substrate. The diffusion layer 5 in the geometrical shape shown in FIG. 2 was incorporated by thick-film technology by means of a screenprinted layer of a mixture of theobromine and coarse-grained $ZrO_2$ having a particle size of 10 micrometers; in the later sintering process in the temperature range of about 300° C., the theobromine evaporated. The $ZrO_2$ solid electrolyte layer 9 was produced by printing with a paste of $ZrO_2$ stabilized with $Y_2O_3$, having a particle size of approximately 1 to 2 micrometers. The printed layer had a thickness of 80 micrometers. The pump electrodes 2 and 3, comprising platinum, were also applied by a known screenprinting technique; a 10-micrometers-thick $Al_2O_3$ isolation layer was applied beforehand to the surface of the solid electrolyte layer carrying the outer pump electrode, in the region of the conductor track of the outer pump electrode. The pump electrodes had a thickness of 12 micrometers. The conductor tracks were produced based on a typical Pt cermet paste comprising 85 part by weight of Pt powder and 15 parts by weight of YSZ powder.

To produce the engobe 11, a paste based on $Al_2O_3$ was printed on. The engobe had a thickness of approximately 30 micrometers.

The cover layer 7 was likewise printed, beginning with a paste based on $Al_2O_3$. It had a thickness of approximately 10 micrometers.

After the application of the electrodes, conductor tracks, isolation layer and engobe and cover layer, the coated substrate was subjected to a sintering process, in which it was heated for approximately 3 hours to a temperature in the range of 1380° C.

After suitable calibration by severing zigzag segments, the sensor element produced was inserted into a housing of the type known from German Patent Disclosure Document 32 06 903 and used to determine the lambda value of gas mixtures. Excellently reproducible results were obtained.

The production of a sensor element according to the invention is preferably done by machine using the multiple printed panel technique. Advantageously, the width of the sensor is approximately 4 to 6 mm. The electrode diameter is advantageously from 3 to 4 mm, for instance 3.6 mm.

We claim:

1. Sensor element for limiting-current sensors to determine the lambda value of gas mixtures, in particular of exhaust gases of internal combustion engines, having
   a solid electrolyte ceramic substrate (1),
   first and second pump electrodes (2, 3) disposed on opposite sides of said solid electrolyte ceramic substrate (1),
   said first pump electrode (2) being accessible for a measurement gas; said gas being supplied to said first pump electrode through a diffusion layer (5) acting as a diffusion barrier and located on said solid electrolyte ceramic substrate adjacent to said first pump electrode;
   said first pump electrode and said diffusion layer having a gas-tight cover layer (7) covering said first pump electrode (2) and the diffusion layer (5) for exclusion of the measurement gas, except for a measurement gas inlet opening (4) located at an edge of said diffusion layer remote from and opposite an edge thereof that adjoins said first pump electrode;
   a first conductor track (2') on said substrate (1) for the first pump electrode (2), said first conductor track being covered by said gas-tight cover layer (7), and
   a second conductor track (3') on said substrate (1) for said second pump electrode (3),
   characterized in that
   the diffusion layer (5) has, at its edge which is nearest to the measurement gas inlet opening (4), a series of outwardly tapered projections, each oriented towards said measurement gas inlet opening, said gas-tight layer filling all gaps between said projections, whereby the finished sensor element is calibratable by at least one mechanical or laser cutting operation which cuts off extremity portions of a plurality of said projections and thereby reduces the diffusion resistance of the diffusion layer.

2. The sensor element of claim 1, characterized in that
   said tapered projection of said edge of said diffusion layer (5) together present a zigzag-contoured edge having equally spaced edge extremities open or openable for producing said measurement gas inlet opening (4) and in that
   the number and spacing from one another of the edge extremities of the zigzag-contoured edge and the length of said tapered projections are selected to optimize the load of said first pump electrode.

3. The sensor element of claim 2,
   characterized in that
   the diffusion layer (5), including said zigzag-profiled edge portion thereof, is printed onto the solid electrolyte ceramic substrate (1) by a screenprinting process.

4. The sensor element of claim 2,
   characterized in that
   the solid electrolyte ceramic substrate (1) comprises $ZrO_2$ stabilized with $Y_2O_3$.

5. The sensor element of claim 1,
   characterized in that the diffusion layer (5) comprises a porous layer consisting essentially of a material selected from the group consisting of $Al_2O_3$ and $ZrO_2$.

6. The sensor element of claim 5,
characterized in that
the solid electrolyte ceramic substrate (1) comprises $ZrO_2$ stabilized with $Y_2O_3$.

7. The sensor element of claim 1,
characterized in that
the diffusion layer (5), including said outwardly tapered edge projections thereof, is printed onto the solid elect ceramic substrate (1) by a screenprinting process.

8. The sensor element of claim 7, characterized in that the solid electrolyte ceramic substrate (91) comprises $ZrO_2$ stabilized with $Y_2O_3$.

9. The sensor element of claim 1,
characterized in that
the solid electrolyte ceramic substrate (1) comprises $ZrO_2$ stabilized with $Y_2O_3$.

10. A sensor element for limiting-current sensors for determining the lambda value of gas mixtures, in particular of exhaust gases of internal combustion engines, comprising:
a ceramic substrate (1),
a diffusion layer (5) on one side of said substrate (1) for producing a permeable diffusion barrier for reducing diffusion of a measurement gas, said diffusion layer (5) covering less than all of said side of said substrate,
an inner pump electrode (2) on a portion of said diffusion layer and having a first conductor track (2') on a portion of said one substrate side which is not covered by said diffusion layer,
a solid electrolyte gas-tight cover layer (9) directly covering said inner pump electrode (2) and portions of said diffusion layer (5) not covered by said inner pump electrode (2) and conformably covering said diffusion layer where it would otherwise be exposed to measurement gas except for a measurement gas inlet opening (12) located at an edge portion of said diffusion layer (5) which is opposite and remote from said inner electrode,
an outer pump electrode (3) on said solid electrolyte gas-tight cover layer (9) connected to a second conductor track (3');
an insulating layer (10) on said solid electrolyte gas-tight cover layer 9 and interposed between said solid electrolyte gas-tight cover layer (9) and said first conductor track (2'), whereby said second conductor track (3') is insulated from said first conductor track (2'), and
a porous engobe layer (11) on said outer pump electrode (3),
characterized in that
said diffusion layer (5) has at the edge thereof at which said measurement gas inlet opening (12) is located, a series of outwardly tapered projections each oriented towards the measurement gas inlet opening (12), said solid electrolyte gas-tight cover layer (9) filling all gaps between said projections whereby the finished sensor element is calibratable by at least one mechanical or laser cutting operation which cuts off extremity portions of a plurality of said outwardly tapered projections and thereby reduces the diffusion resistance of the diffusion layer.

11. The sensor element of claim 10, wherein a gas-tight layer (7) of $Al_2O_3$ base is provided covering said second conductor track (3') and wherein said solid electrolyte cover layer (9) extends above said first conductor track (2') beneath said insulating layer (10).

12. The sensor element of claim 10, wherein the presence of said projections provides a configuration of said edge of said diffusion layer remote from said inner pump electrode which has a zigzag-profile and wherein said projections have equally spaced extremities.

13. The sensor element of claim 12,
characterized in that
the diffusion layer (5) comprises a porous layer consisting essentially of a material selected from the group consisting of $Al_2O_3$ and $ZrO_2$.

14. The sensor element of claim 12,
characterized in that
the diffusion layer (5), including said tapered projections, is printed into the ceramic substrate (1) by a screening process.

15. The sensor element of claim 12,
characterized in that
the ceramic substrate (1) comprises $ZrO_2$ stabilized with $Y_2O_3$.

16. The sensor element of claim 10, characterized in that the diffusion layer (5) comprises a porous layer consisting essentially of a material selected from the group consisting of $Al_2O_3$ and $ZrO_2$.

17. The sensor element of claim 10,
characterized in that
the diffusion layer (5), including said tapered projections, is printed onto the ceramic substrate (1) by a screenprinting process.

18. The sensor element of claim 10,
characterized in that
the ceramic substrate (1) comprises $ZrO_2$ stabilized with $Y_2O_3$.

* * * * *